United States Patent
Pruitt et al.

(10) Patent No.: US 12,186,470 B1
(45) Date of Patent: Jan. 7, 2025

(54) MEDICAL NEEDLE PLACEMENT DEVICE AND METHODS OF USING THE SAME

(71) Applicant: Navigator Medical, LLC, Memphis, TN (US)

(72) Inventors: McKenna M. Pruitt, Memphis, TN (US); Emily M. Kerivan, Scottsdale, AZ (US); Kade D. Frisby, Pass Christian, MS (US); Jordan M. Kocsis, Johnstown, PA (US)

(73) Assignee: Navigator Medical, LLC, Memphis, TN (US)

( * ) Notice: Subject to any disclaimer, the term of this patent is extended or adjusted under 35 U.S.C. 154(b) by 0 days.

(21) Appl. No.: 18/639,152

(22) Filed: Apr. 18, 2024

Related U.S. Application Data

(60) Provisional application No. 63/460,668, filed on Apr. 20, 2023.

(51) Int. Cl.
*A61M 1/36* (2006.01)
*A61M 25/00* (2006.01)
*A61M 25/02* (2006.01)

(52) U.S. Cl.
CPC ........ *A61M 1/3661* (2014.02); *A61M 1/3655* (2013.01); *A61M 2025/0091* (2013.01); *A61M 2025/028* (2013.01); *A61M 2205/583* (2013.01)

(58) Field of Classification Search
CPC .... A61M 2025/028; A61M 2025/0091; A61M 5/425; A61M 5/427; A61M 5/46; A61M 1/3655; A61M 1/3661; A61M 25/06; A61M 25/02; A61B 90/11
See application file for complete search history.

(56) References Cited

U.S. PATENT DOCUMENTS

| | | | | |
|---|---|---|---|---|
| 2,008,340 A | * | 7/1935 | Salvati | A61M 25/02 604/174 |
| 2,245,350 A | * | 6/1941 | Marshall | A61M 5/427 604/116 |
| 2,402,306 A | * | 6/1946 | Turkel | A61M 25/02 600/573 |
| 4,332,248 A | * | 6/1982 | DeVitis | A61M 5/425 604/179 |
| 5,292,325 A | * | 3/1994 | Gurmarnik | A61M 5/427 606/1 |
| 5,911,707 A | * | 6/1999 | Wolvek | A61M 5/3287 604/116 |
| 2013/0041318 A1 | * | 2/2013 | Vosseler | A61M 5/3293 604/117 |

(Continued)

*Primary Examiner* — Theodore J Stigell
(74) *Attorney, Agent, or Firm* — Foley IP Law, PLLC

(57) ABSTRACT

A device for positioning and inserting a medical needle assembly into a patient. The device includes a base configured to be placed adjacent to a needle insertion site on the patient which includes a plurality of positioning features configured to be used for positioning and aligning the device on the patient. The device includes a needle channel and a needle guidance protrusion disposed on the top of the base. The needle guidance protrusion includes a sloped surface having a first end disposed adjacent to the needle channel and a second end displaced from the first end and is sloped such that the second end is disposed higher than the first end. A needle assembly is configured to be pushed down the sloped surface such that the needle of the needle assembly travels through the needle channel to the needle insertion site.

16 Claims, 11 Drawing Sheets

(56) References Cited

U.S. PATENT DOCUMENTS

| | | | |
|---|---|---|---|
| 2013/0131467 A1* | 5/2013 | Deck | A61B 17/3403 600/309 |
| 2015/0157787 A1* | 6/2015 | Cully | A61M 5/46 604/117 |
| 2016/0367766 A1* | 12/2016 | Baker | A61M 5/3287 |
| 2024/0165333 A1* | 5/2024 | Hoffer | A61M 5/24 |

* cited by examiner

MEDICAL NEEDLE PLACEMENT DEVICE AND METHODS OF USING THE SAME

CLAIM OF PRIORITY TO PRIOR APPLICATION

This application claims priority to U.S. Provisional Patent Application No. 63/460,668, filed on Apr. 20, 2023, the entire disclosure of which is incorporated herein by reference.

FIELD OF THE INVENTION

The present invention relates generally to devices for guiding placement and insertion of medical needles into patients, and more particularly to devices for guiding placement and insertion of medical needles for performing buttonhole techniques for dialysis treatments.

BACKGROUND OF THE INVENTION

Throughout the medical industry, practitioners are tasked with inserting needles into their patients in very precise locations for performing various medical activities. Often, for various activities, the practitioner must provide repeated needle insertions to a patient in a consistent location. One such medical procedure in which this is prevalent is in dialysis treatments.

Dialysis is the process of removing toxins and other undesirable elements from the blood of patients whose kidneys have failed and can no longer perform their proper blood cleansing functions. A common way dialysis is performed is by inserting a needle into an arteriovenous (AV) fistula of the patient to draw blood out of the patient, which is then sent through a dialysis machine for treatment, and ultimately returned to the patient at the AV fistula. Dialysis patients must have this treatment performed multiple times a week, often for their entire lives, or at least until they can undergo a kidney transplant. Thus, the continued needle poking of the AV fistula for these patients can cause severe scar tissue and can ultimately cause the AV fistula to fail. As those with skill in the art will recognize, the failure of the AV fistula is obviously detrimental, as the patient is then required to have surgery to form another AV fistula, and there are only a limited number of sites on a patient where an AV fistula can be created.

A technique currently in use to curtail the chance of damaging the AV fistula for dialysis patients is called the buttonhole technique. The buttonhole technique involves a skilled practitioner inserting a sharp dialysis needle into the same puncture location at the same insertion angle over the span of numerous treatment sessions until a tunneled track is created in the patient's skin. Eventually, this tunnel becomes formed enough that a practitioner can insert a dull dialysis needle through this tunnel (i.e. a "buttonhole") for performing the dialysis treatment, which is much less painful than creating a new puncture with a sharp needle for every treatment, and also prevents unnecessary damage to the AV fistula. Unfortunately, the buttonhole technique is not commonly used, partially because it requires an incredibly skilled practitioner to insert the sharp needle repeatedly over many sessions into the same puncture point and at the same angle of insertion in order to form a viable buttonhole puncture.

Accordingly, there has been a long-felt need for devices and methods for consistently forming buttonhole punctures for dialysis patients.

BRIEF SUMMARY OF THE INVENTION

According to various embodiments of this disclosure, disclosed is a device for positioning and inserting a needle assembly into a patient. The device includes a base including a bottom surface configured to contact the skin of the patient, a top surface opposite of the bottom surface, a front end configured to be placed adjacent to a needle insertion site of the patient, a rear end opposite of the front end, and a plurality positioning features configured to be used for positioning and aligning the device on the patient. The device includes a needle channel disposed on the top surface adjacent to the front end and comprising a channel outlet facing the front end and a channel inlet opposite the channel outlet. The device includes a needle guidance protrusion disposed on the top surface and including a sloped surface having a first end disposed adjacent to the channel inlet and a second end displaced from the first end toward the direction of the rear end of the base, wherein the sloped surface is sloped at a slope angle such that the second end is disposed at a greater elevation from the top surface of the base than the first end. Where the needle assembly is configured to be placed on the sloped surface and pushed down the sloped surface such that a needle of the needle assembly travels through the needle channel to the needle insertion site to form an insertion puncture in the skin of the patient According to various embodiments, the slope angle is substantially between 20 and 35 degrees from the base. According to various embodiments, the needle guidance protrusion further comprises a convex rounded section extending from the second end of the sloped surface to the rear end of the base, where a tube of the needle assembly is configured to be placed along a top of the convex rounded section. According to various embodiments, the convex rounded section comprises a first convex section extending from the second end of the sloped section; a second convex section extending from the first convex section and being more rounded than the first convex section, wherein the second convex section comprises the apex of the needle guidance protrusion; and a tail section extending from the second convex section towards the rear end of the base, wherein the tail section is relatively flat in comparison to the first and second convex sections. According to various embodiments, the sloped surface comprises a concave top surface for receiving the needle assembly, wherein the concave top surface is concave about a length axis of the sloped surface. According to various embodiments, the bottom surface is concave about an axis spanning from the front end of the base to the rear end of the base to accommodate the curvature of the body part of the patient on which the device is placed. According to various embodiments, the bottom surface comprises, or is configured to be used with, an adhesive for adhering the device to the skin of the patient.

According to various embodiments, the base has a generally circular cross-section. According to various embodiments, each of the plurality of positioning features is a through-hole spanning from the top surface to the bottom surface of the base, and each of the plurality of through-holes is sized to allow for a user to pass a marking device through the through-hole and create a mark on the skin of the patient associated with the through-hole. According to various embodiments, the plurality of through-holes are positioned on the base such that aligning each of the through-holes with an associated and previously-made mark of the through-hole results in the device being positioned on the user in a place proper for using the device to insert the needle assembly into the insertion puncture. According to various embodiments, there are three of the plurality of through-holes; two of the plurality of through-holes are disposed on a first side of the needle guidance protrusion; and one of the plurality of through-holes is disposed on a second side of the needle guidance protrusion.

According to various embodiments, the channel outlet has a smaller diameter than the channel inlet; the channel outlet is part of a channel cylindrical section of the needle channel; and the channel inlet is part of a conical section of the needle channel, wherein the conical section is configured to reduce the diameter of the needle channel from the diameter of the channel inlet to the diameter of the channel outlet. According to various embodiments, the needle channel is disposed in a channel block disposed on the top surface of the base adjacent to the front end of the base. According to various embodiments, the channel block has a convex round top surface. According to various embodiments, the device is formed from a single piece of plastic material.

According to various embodiments of this disclosure, disclosed is a method of positioning and inserting a needle assembly into a patient using a needle placement device. The method includes performing an initial session of a medical activity involving the use of the needle assembly, including placing a bottom surface of a base of the needle placement device on the patient with a front end of the base adjacent to a desired needle insertion site on the patient, placing the needle assembly on a sloped surface of a needle guidance protrusion of the needle placement device, pushing the needle assembly down the sloped surface to push a needle of the needle assembly through a needle channel of the needle placement device disposed adjacent to the front end of the base to ultimately insert the tip of the needle into the insertion site to form an insertion puncture with the needle in the skin of the patient at an angle of insertion defined by the sloped surface, marking, using a marking device, adjacent to each of a plurality of positioning features on the base to create a mark on the patient's skin associated with each of the plurality of marking features, performing the medical activity on the patient using the needle inserted in the insertion puncture, and removing the needle from the insertion puncture and the needle placement device in response to the medical activity being completed. The method further includes performing a subsequent session associated with the medical activity, including placing the needle placement device on the patient by aligning each of the plurality of positioning features with its associated mark made on the patient's skin in the initial session, and repeating various steps performed in the initial session to ensure the needle is inserted into the same insertion puncture at the same angle of insertion as performed in the initial session.

According to various embodiments, the medical activity is dialysis treatment and the insertion puncture is formed on an AV fistula of the patient. According to various embodiments, the method is repeated to transform the insertion puncture into a buttonhole puncture in the skin to allow for a dull dialysis needle to be inserted into the buttonhole puncture. According to various embodiments, the method is performed for each of a first needle assembly configured to draw the patient's blood from the AV fistula for dialysis treatment; and a second needle assembly configured to return the treated blood back to the AV fistula.

DETAILED DESCRIPTION OF THE INVENTION

The following descriptions relate to presently preferred embodiments and are not to be construed as describing limits to the invention, whereas the broader scope of the invention should instead be considered with reference to the claims, which may be now appended or may later be added or amended in this or related applications. Unless indicated otherwise, it is to be understood that terms used in these descriptions generally have the same meanings as those that would be understood by persons of ordinary skill in the art. It should also be understood that terms used are generally intended to have the ordinary meanings that would be understood within the context of the related art, and they generally should not be restricted to formal or ideal definitions, conceptually encompassing equivalents, unless and only to the extent that a particular context clearly requires otherwise.

For purposes of these descriptions, a few wording simplifications should also be understood as universal, except to the extent otherwise clarified in a particular context either in the specification or in particular claims. The use of the term "or" should be understood as referring to alternatives, although it is generally used to mean "and/or" unless explicitly indicated to refer to alternatives only, or unless the alternatives are inherently mutually exclusive. When referencing values, the term "about" may be used to indicate an approximate value, generally one that could be read as being that value plus or minus half of the value. "A" or "an" and the like may mean one or more, unless clearly indicated otherwise. Such "one or more" meanings are most especially intended when references are made in conjunction with open-ended words such as "having," "comprising" or "including." Likewise, "another" object may mean at least a second object or more.

The following descriptions relate principally to preferred embodiments while a few alternative embodiments may also be referenced on occasion, although it should be understood that many other alternative embodiments would also fall within the scope of the invention. It should be appreciated by those of ordinary skill in the art that the techniques disclosed in these examples are thought to represent techniques that function well in the practice of various embodiments, and thus can be considered to constitute preferred modes for their practice. However, in light of the present disclosure, those of ordinary skill in the art should also appreciate that many changes can be made relative to the disclosed embodiments while still obtaining a comparable function or result without departing from the spirit and scope of the invention.

Figure 1:
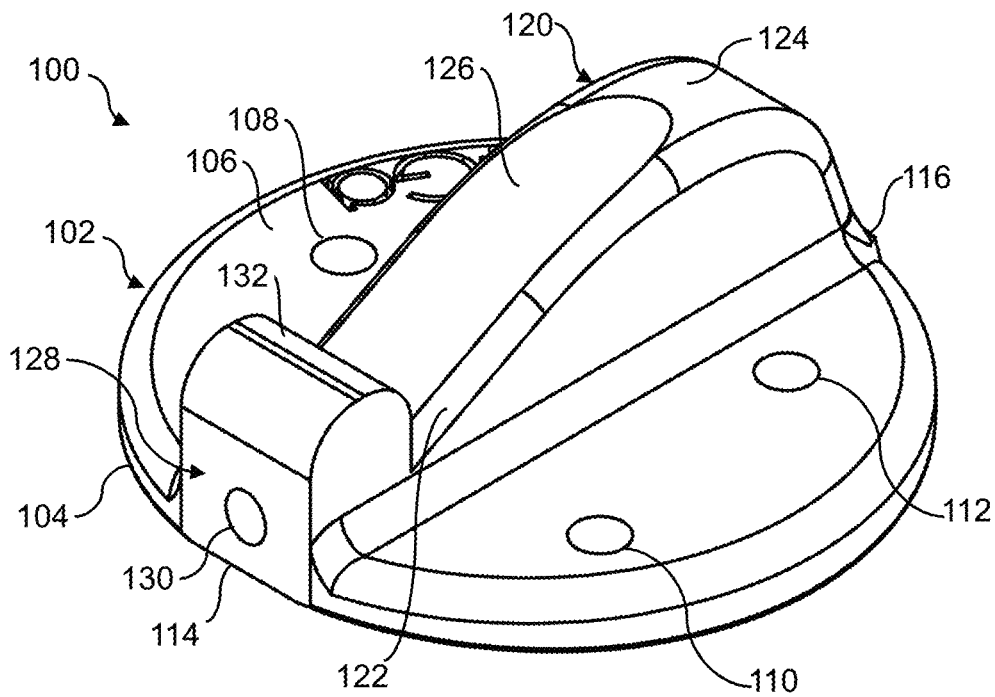
FIG. 1 illustrates a perspective view of a medical needle placement and insertion device, according to an embodiment of this disclosure.

FIG. 1 illustrates a perspective view of a medical needle placement and insertion device 100, according to an embodiment of this disclosure. As will become clearer throughout the reading of this detailed description, device 100 is configured to be used by a medical practitioner in performing a medical procedure or activity on a patient that requires a needle to be inserted into the patient. Specifically, device 100 is configured to be used so that the practitioner can perform the medical procedure over a span of multiple treatment sessions at a same and consistent needle insertion puncture point on a patient at a consistent insertion angle. Specifically, in some embodiments, device 100 is used by a practitioner in the dialysis treatment of the patient and is used in performing the buttonhole technique. The buttonhole technique requires the practitioner to insert a sharp dialysis needle into the same puncture location of the AV fistula at the same insertion angle over and over until a tunneled track is created in the patient's skin. Eventually, this tunnel becomes formed enough that a practitioner can insert a dull dialysis needle through this tunnel (i.e. a "buttonhole"), which is much less painful than creating a new puncture with a sharp needle for every treatment, and also prevents damage to the patient's AV fistula.

Device 100 has a base 102 with a bottom surface 104 configured to be placed on a patient for use of device 100, and a top surface 106 opposite the bottom surface. As shown, base comprises 102 a generally circular overall shape and cross-section, but those with skill in the art will understand that device 100 incorporates bases 102 of various size and shape according to various embodiments of this disclosure. Base 102 comprises a plurality of alignment and positioning features 108-112 configured to be used in positioning and aligning the device 100 on the patient. Specifically, in some embodiments, features 108-112 are through-holes 108-112 spanning from top surface 106 to bottom surface 104. As will be discussed in greater detail below, after placing device 100 at a desired location on a patient, a practitioner is configured to pass a marking device (i.e., pen, permanent marker, medical marker, medical tattoo pen, etc.) through each of the through-holes 108-112 a form an associated mark for each hole 108-112 on the patient's skin. That way, in a subsequent use of device 100, the practitioner can align each through hole 108-112 with its associated mark on the skin so that device 100 can be positioned and aligned in the same orientation as it was in the previous use of the device 100, and thus provide for a needle assembly to be inserted into the patients at a same needle puncture point of the patient. Base 102 has a front end 114 configured to be placed adjacent to the needle insertion site of the patient, and a rear end 116, opposite of front end 114.

Device 100 further includes a needle insertion protrusion 120 disposed on top surface 106, comprising a sloped section 122 and a convex rounded section 124. Additionally, protrusion 120 comprises a top concave surface 126 formed on the sloped section 122 and extending into part of the rounded section 124. As shown, concave surface 126 is generally concave about a length axis of the sloped section 122, the length axis extending generally from front end 114 to rear end 116 along the sloped angle of section 122. Surface 126 is concave in nature for receiving a needle assembly, as will be discussed in greater detail below. Device 100 further comprises needle channel block 128 disposed on the top surface 106 at the front end 114 of base 102. Block 128 comprises a needle channel 130 passing through block 128 and thus providing access from protrusion 120 to an insertion site adjacent to front end 114. As shown, in some embodiments, block 128 has a convex rounded top surface 132. As will be discussed in greater detail below, in use, a practitioner places a needle assembly on surface 126 with the distal end or tip of a needle of the needle assembly facing channel 130. The practitioner then pushes the needle assembly down surface 126 along sloped section 124 so as to push the distal end of the needle through channel 130, and eventually into a needle insertion puncture on the skin of the patient adjacent to front end 114.

Figure 2:
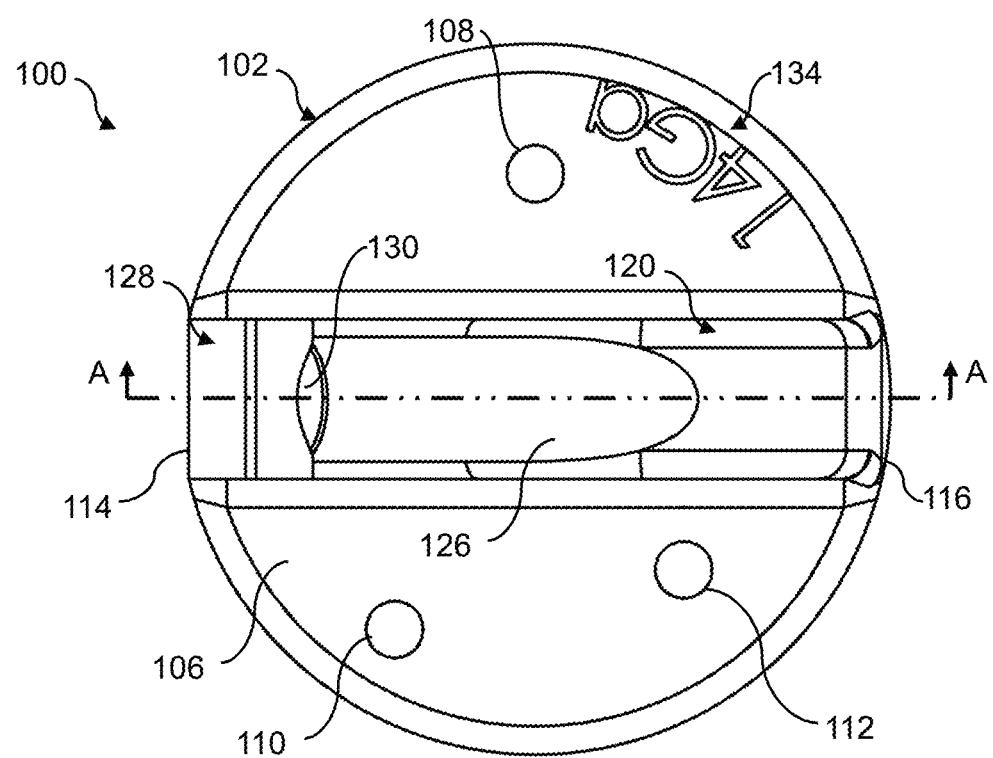
FIG. 2 illustrates a top view of the device of FIG. 1.

FIG. 2 illustrates a top view of device 100. FIG. 2 illustrates the substantially circular nature of base 102. However, as previously discussed, base 102 can comprise various shapes without departing from the scope of this disclosure. Also shown in better detail is the placement of each hole 108-112 on base 102. Hole 108 is positioned on a first side of protrusion 120, while holes 110, 112 are positioned on a second side of protrusion 120. As previously discussed, and as will be covered in greater detail below, each hole 108-112 is meant to be aligned with a mark on the skin of the patient made by sticking a marking device through the specific hole 108-112 during a previous use of device 100, and thereby ensure the device is positioned on the patient in the same location and orientation as it was for the previous use of the device 100. Holes 108-112 are strategically positioned on base 102 such that, in order for each hole 108-112 to be aligned with its associated mark on the skin, the device must be positioned in the same position and the same orientation as it was when the mark was made. As shown, there must be at least three holes 108-112 for performing this functionality. For example, if base 102 only had two holes (such as only holes 108 and 110, for example), the two holes could each be aligned on a mark both when the device 100 is in the correct orientation and also when the device 100 is rotated 180 degrees from the correct orientation. As shown, the three holes 108-112 effectively form a triangle with uneven side such that the only way all holes 108-112 can be simultaneously aligned with a previously made mark on the skin is when the device 100 is in the same position and orientation as it was for the previous use. One with skill in the art will understand that, according to various embodiment of this disclosure, base 102 comprises more than the three through-holes 108-112 described. Additionally, although perhaps not always ideal, according to various embodiments, device includes less than the three through-holes 108-112 described.

Although through-holes are shown as being used as alignment and positioning features 108-112, those with skill in the art will understand that various feature types can be used as alignment and positioning features 108-112 according to various embodiment of this disclosure. For example, in some embodiments, base 102 can have three positioning arrows (such as arrows 408-412, discussed in greater detail in FIG. 15) placed along the outer edge of base 102. Once in a position, the practitioner can form a mark on the skin along the edge of base 102 adjacent to each arrow. Thus, in subsequent uses of device 100, each arrow of the base 102 can be aligned with its associated, previously-made mark, for positioning and aligning device 100, much in the same way holes 108-112 are aligned with their associated marks, as has been described and will continue to be described below. Accordingly, those with skill in the art will recognize that, although through-holes are depicted, various feature-types can be used for positioning and alignment features 108-112 according to various embodiments of this disclosure.

As shown, according to various embodiments, device 100 further comprises a label 134 labeling what gauge size of needle the device 100 is meant to be compatible with. As shown, the device illustrated is meant to be used with a 14-gauge needle. A practitioner may have access to a plurality of devices 100, each meant to be compatible with a different sized needle. For example, various embodiments of the device herein are meant to be compatible with needles ranging in size from 14- to 17-gauge. However, devices compatible with needles sized larger than 14-gauge and smaller than 17-gauge are included as part of this disclosure. In addition to identifying which of a plurality of the devices 100 is appropriate for a needle based on labeling 134, in some embodiment, the various devices 100 are color-coded. For example, device 100 meant for a 14-gauge needle may be red, while a device for a 15-gauge needle may be blue, and so on. That is to say, in a system of devices 100, each device 100 can have its own unique color based on the needle size it is meant to be compatible with, which simplifies identifying the correct device for a given treatment for a practitioner.

Figure 3:
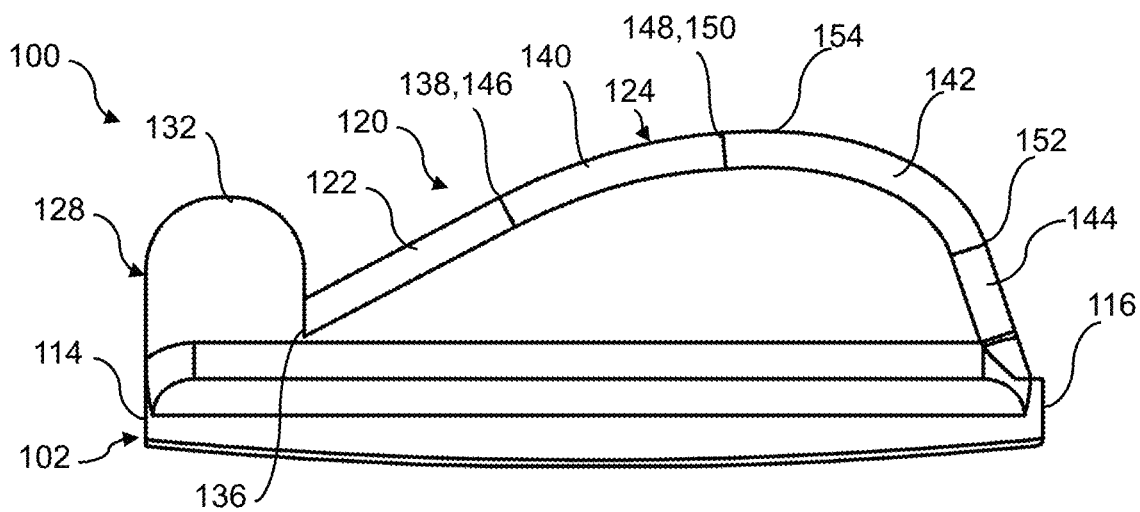
FIG. 3 illustrates a left side view of the device of FIG. 1.

FIG. 3 illustrates a left side view of device 100. From FIG. 3, the structure of protrusion 120 can be better understood. As previously discussed, protrusion comprises a sloped section 122 and a convex rounded section 124. The sloped section 122 has a first end 136 disposed adjacent to block 128 and channel 130, and a second end 138 opposite the first end 136 along the length of the sloped section 122. Due to the sloped nature of section 122, second end 138 is disposed at a greater elevation from base surface 106 than first end 136. Rounded section 124 comprises a first convex section 140, a second convex section 142, and a tail section 144. As shown, first convex section 140 has a first end 146 adjacent end 138 and extends towards rear end 116 to a second end 148 of first convex section 140. Section 140 is rounded such that second end 148 is elevated a greater distance from top surface 106 than first end 146. As shown, second convex section 142 has a first end 150 adjacent to end 148 and extends towards rear end 116 to a second end 152 of first convex section 142. Section 142 is rounded and convex so as to define the apex point 154 of the protrusion, which is the point of the protrusion 120 having the greatest elevation from top surface 106. Second section 142 is more rounded, or has a greater degree of convexity, than first convex section 140. Said another way, first convex section 140 acts as a transition from the flat nature of sloped section 122 to the second convex section 142, which has the greatest degree of convexity of the protrusion 120. Tail section 144 extends from end 152 to rear end 116. As shown, tail section 144 is sloped section connecting end 152 and rear end 116. Tail section 144 is relatively flat compared to first and second convex sections 140, 142.

As will be discussed in greater detail below, in use, a needle assembly is seated in concave surface 126 of sloped section 122, and tubing coming from the needle assembly (such as for blood draws/injections) is meant to be draped and seated along the top of rounded section 124. The rounded section 124 provides a smooth transition from the needle assembly so that the weight of the tubing does not tug on the needle in the patient's skin and thereby cause discomfort or damage. Device 100 incorporates various smooth and rounded features, such as the features described above related to protrusion 120 as well as the convex top 132 of block 128, to prevent any unintentional snagging by the device 100 on associated pieces of medical equipment, such as needle tubing.

Figure 4:
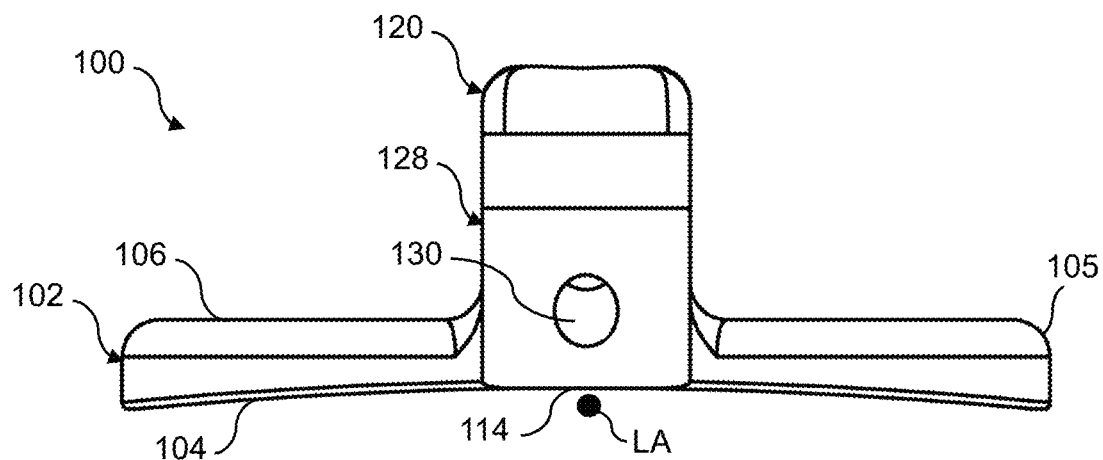
FIG. 4 illustrates a front view of the device of FIG. 1.
Figure 5:
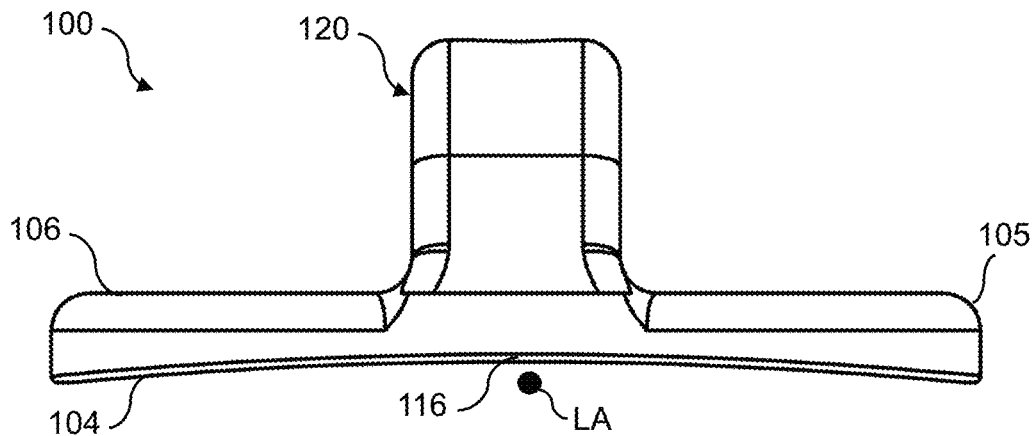
FIG. 5 illustrates a rear view of the device of FIG. 1.

FIGS. 4 and 5 illustrate front and rear views, respectively, of device 100. Base 102 incorporates a rounded edge 105 between bottom surface 104 and top surface 106 to prevent any unintentional snagging of device 100. As shown, in some embodiments, bottom surface 104 is generally curved in nature. As shown, in some embodiments, bottom surface 104 is a rounded, concave surface. Specifically, in the illustrated embodiment, bottom surface 104 is rounded about a length axis LA of device 100 extending from the front end 114 to the rear end 116. Surface 104 is rounded to accommodate the convex curvature of the part of the patient's body on which device 100 is configured to be placed. For example, in some embodiments, device 100 is configured to be placed on a patient's forearm in an orientation such that the length of the forearm is substantially aligned with length axis LA. As such, the convex nature of the forearm follows the concave nature of bottom surface 104 so as to comfortably fit such that bottom surface 104 can, in effect, "grip" the forearm. Although device 100 shows bottom surface 104 being concave about length axis LA, various other embodiments of this disclosure include bottom surfaces having curved or concave features in other positions on the bottom surface 104, based upon the body part of the patient on which the device is meant to be placed in use. For example, according to some embodiments, the device is configured to be used on the leg of a patient, and the bottom surface of the device 100 is curved or concave according to the convex curvature of the portion of the leg where the device is meant to be used.

According to various embodiments, bottom surface 104 incorporates additional features to better "grip" the patient. In some embodiments, the bottom surface 104 has a greater coefficient of friction than the rest of the device 100. In some embodiments, the bottom surface is made from or incorporates rubber or is configured to be coupled with rubber features for better adhering to the skin of the patient. In some embodiments, the bottom surface 104 has an integrated adhesive for gripping the patient. In some embodiments, a replaceable adhesive, such as, for example, double-sided medical tape medical glue, or another medical adhesive is configured to be applied to the bottom surface 104.

Figure 6:
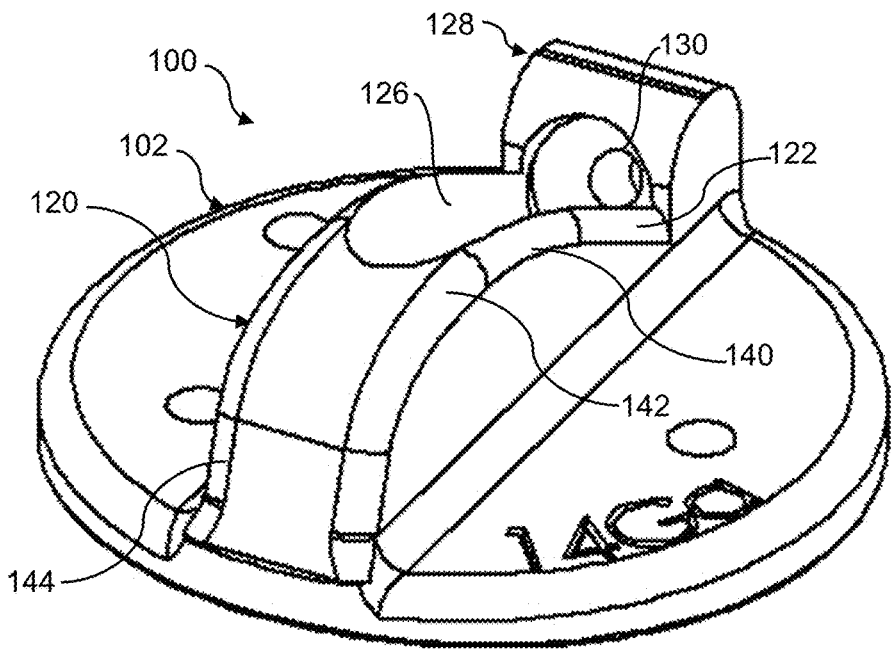
FIG. 6 illustrates a rear perspective view of the device of FIG. 1.

FIG. 6 illustrates a rear perspective view of device 100. FIG. 6 illustrates how the concave top surface 126 of sloped section 122 extends from sloped section 122, through first convex section 140, and into second convex section 142. As shown, the top surface of second convex section 142 not occupied by concave section 126, as well as the top surface of tail section 144, are slightly concave to accommodate the seating of the tubing associated with the needle assembly, which has been previously discussed, and will be discussed in greater detail below.

Figure 7:
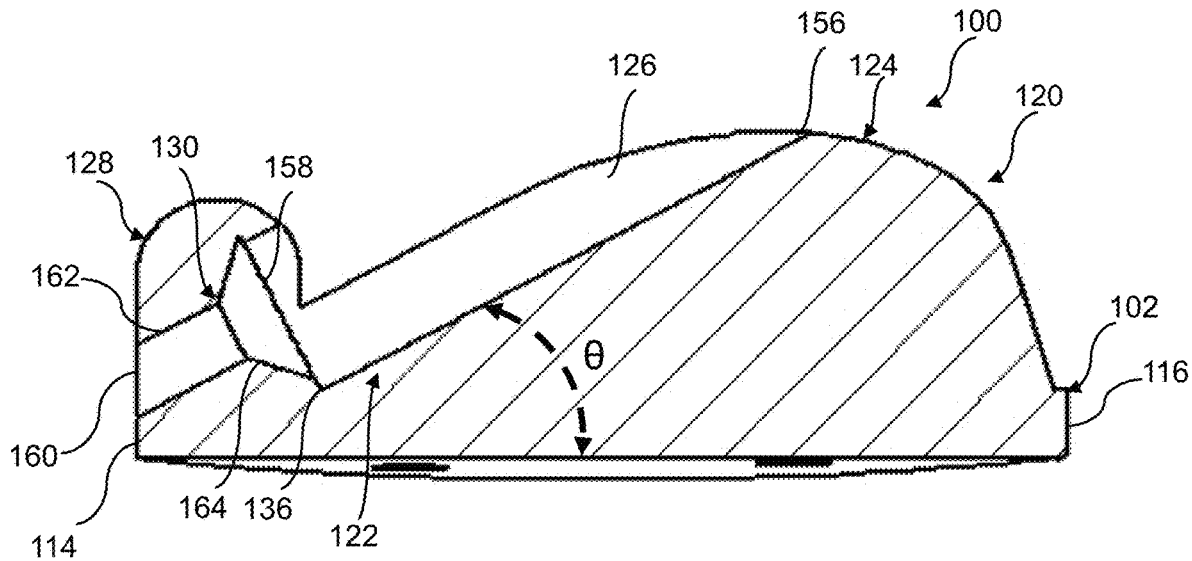
FIG. 7 illustrates a cut view of the device taken along line AA of FIG. 2.

FIG. 7 illustrates a cut view taken along section line A-A shown in FIG. 2. FIG. 7 illustrates the concave surface 126 of sloped surface 122. Specifically, sloped surface 122, and thus concave surface 126, are sloped at a desired needle insertion angle θ from the base 102. The first end 136 of sloped section 122 is also the first end of concave surface 126 and is disposed adjacent to channel 130. The second end 156 of concave surface extends from first surface 136 along protrusion 120 in the direction of the rear end 116 along the angle θ. In some embodiments, second end 156 is disposed on the top surface of second convex section 142. In some embodiments, second end 156 is disposed at the apex point 154.

Needle channel 130 comprises a needle inlet 158 adjacent to sloped section first end 136, and a needle outlet 160, opposite the inlet 158, and adjacent to base front end 114. Outlet 160 is part of a cylindrical section 162 of channel 130, and inlet 158 is part of a conical section 164 of channel 130. As shown, inlet 158 has a larger diameter than outlet 160 and cylindrical section 162, and, thus, the diameter of channel 130 from inlet 158 to cylindrical section 162 is reduced by conical section 164.

From FIG. 7, the use of device 100 with a needle assembly can be further comprehended. Specifically, for dialysis and similar treatments requiring needle insertion into a patient, the hub and needle shaft of a dialysis needle assembly is first placed on concave surface 126, which can be sized/rounded for receiving the hub. The needle assembly can then be pushed down the sloped of section 122 defined by angle θ along the sloped surface 126, thereby pushing the distal end or tip of the needle through channel inlet 158, though funnel section 164, and into cylindrical section 162. The needle assembly can continue to be pushed until the distal end of the need is pushed out of channel 130 through outlet 160 until the distal end of the needle or is inserted into the skin of the patient. In some embodiments, the needle assembly is pushed until the hub of the needle assembly contacts inlet 158 or funnel section 164. In some embodiments, funnel section 164 is sized for receiving the hub of the needle assembly, and the hub of the needle assembly is configured to be seated in conical section 164.

Accordingly, as will be understood by those with skill in the art, the angle of insertion of the needle assembly is set and defined by the insertion angle θ of section 122 and surface 126. The insertion angle θ can thus be set to be an angle determined to be optimal for inserting a needle for a given medical procedure. For example, for dialysis treatment, and specifically for performing the buttonhole technique, it has been found that it is optimal to insert the dialysis needle into the AV fistula of the patient at 20-35 degree angle. Accordingly, in various embodiments insertion angle θ is between 20-35 degrees. Specifically, in some preferred embodiments, insertion angle θ is substantially 27.5 degrees. In some embodiments, insertion angle θ can be between 15-45 degrees. However, those with skill in the art will recognize that insertion angle θ can be greater than 45 degrees or less than 15 degrees without departing from the scope of this disclosure.

According to various embodiments, the diameter of cylindrical section 162, and thus outlet 160, can be sized according to the needle size that the specific device 100 is configured to be used with. That is to say, the cylindrical section 162 can be sized for accepting a needle of a certain size or gauge, but will not accept a needle of a greater size or gauge than what the device 100 is designed to be compatible with. As an example, those with skill in the art will recognize a 14-gauge medical needle has an outer diameter (OD) of approximately 0.083 inch. Accordingly, in embodiments where device 100 is meant to be used with a 14-gauge needle, the diameter of cylindrical section 162 may be large enough for accepting a 14-gauge needle, but not large enough for accepting a 13-gauge needle. For example, in various embodiments, cylindrical section 162 has a 0.0855 inch diameter, which would accept a 14-gauge needle, but would not accept a 13-gauge needle (which has an OD of 0.095 inch, greater than the diameter of section 162). In this way, cylindrical section 162 is configured to act as a partial means of identifying the correct device 100 for a given needle, in addition to the labeling 134 and color coding previously discussed.

Some preferred embodiments include devices 100 meant to be used with needles ranging in size from 14-gauge to 17-gauge, and in such embodiment, the diameter of section 162 can range substantially from 0.0855 inch to 0.0605 inch. Specifically, in some preferred embodiments, the diameter of cylindrical section 162 of a device 100 configured to be used with a 14-gauge is 0.0855 inch; the diameter of cylindrical section 162 of a device 100 configured to be used with a 15-gauge is 0.075 inch; the diameter of cylindrical section 162 of a device 100 configured to be used with a 16-gauge is 0.0675 inch; and the diameter of cylindrical section 162 of a device 100 configured to be used with a 17-gauge is 0.0605 inch. While these are some preferred embodiments, those with skill in the art will understand that devices 100 configured to be used with any medical needle size fall within the scope of this disclosure. For example, according to various embodiments, cylindrical section 162 is sized to work with a medical needle ranging in size anywhere from a 10-gauge (which has a 0.13 inch nominal OD) to a 34-gauge needle (which has a 0.006 inch nominal OD). Additionally, in some embodiments, device 100 has a cylindrical section 162 sized so as to be compatible with multiple different needle sizes rather than just a single specific needle size.

Figure 8:
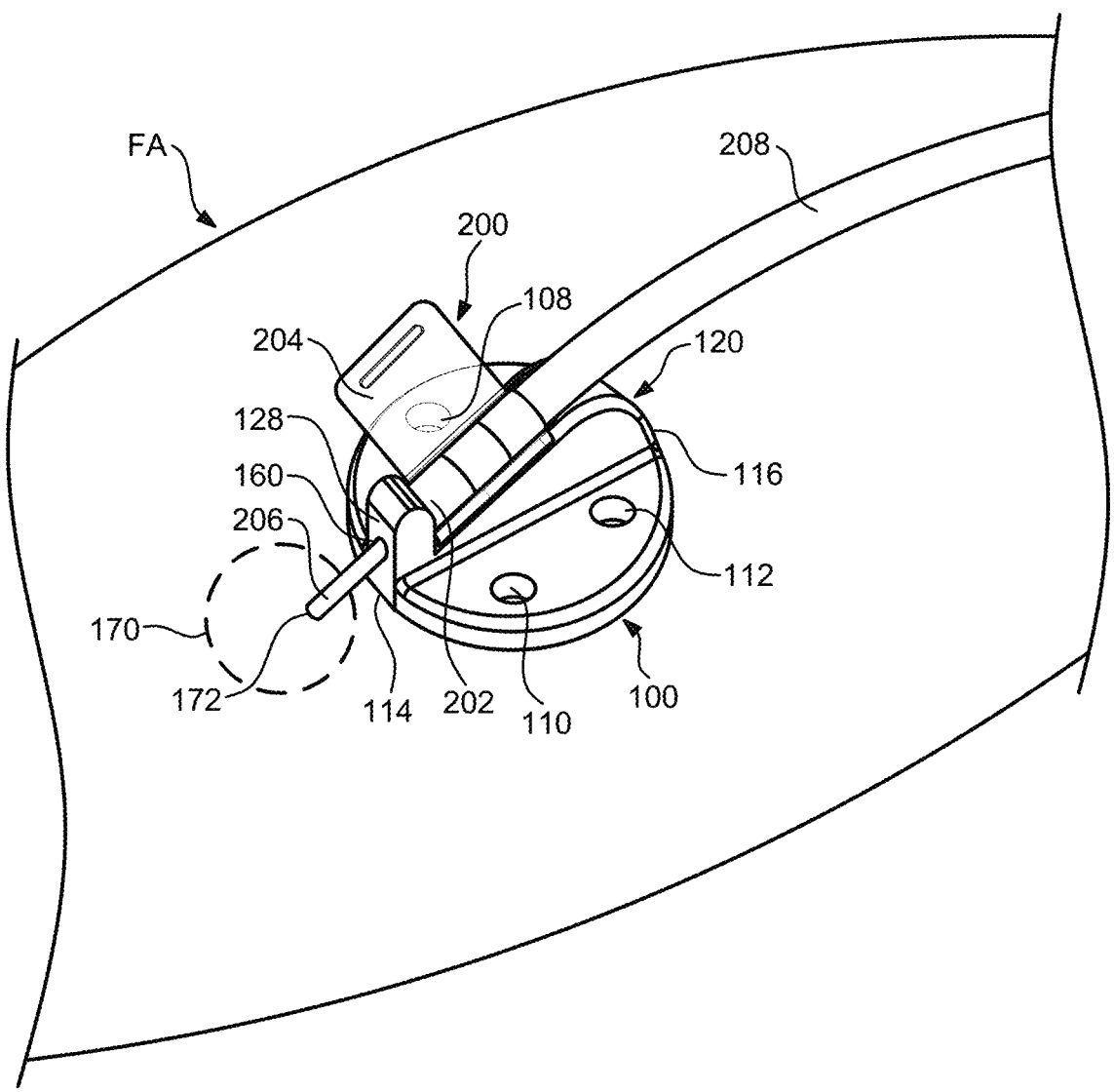
FIG. 8 illustrates the device of FIG. 1 in use on a patient with a needle assembly.
Figure 9:
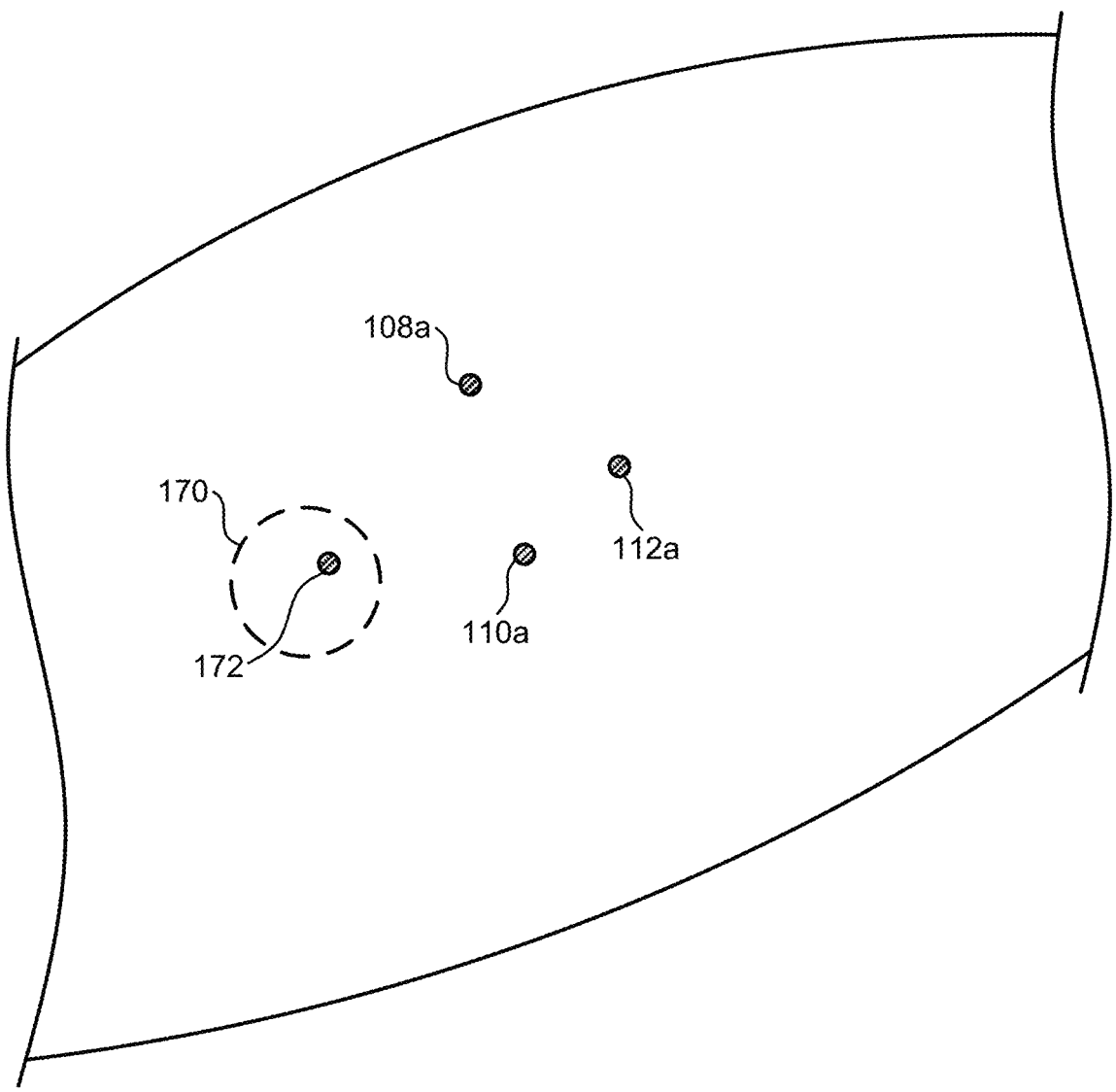
FIG. 9 illustrates a view of the needle insertion site of the patient after the device of FIG. 1 has been used.

FIG. 8 illustrates device 100 being used with a dialysis needle assembly 200 on the forearm FA of a patient for performing treatment on the patient, and FIG. 9 illustrates the forearm FA after device 100 and needle assembly 200 have been removed after completing the treatment. Referring to FIG. 8 (along with the various features of device 100 previously identified and discussed in FIGS. 1-7), bottom surface 104 is placed on the inner part of the forearm of the patient adjacent to a needle insertion site, which identified using the dashed-line circle 170. For example, in a dialysis treatment, the desired insertion site 170 is a part of the skin of the forearm above the AV fistula of a patient. One positioned, the practitioner can pass a marking device through each of holes 108-112 to form marks on the skin associated with each hole 108-112. Specifically, briefly referencing FIG. 9, the practitioner passes the marking device through hole 108 to form mark 108a on the skin; the practitioner passes the marking device through hole 110 to form mark 110a on the skin; and the practitioner passes the marking device through hole 112 to form mark 112a on the skin. As has been discussed above, and will be discussed in greater detail below, marks 108a-112a are used by the practitioner in aligning the device 100 for a subsequent treatment in the same position and orientation as shown in FIG. 8. To insert the needle into the insertion site 170, the needle assembly hub 202 and/or wing section 204 is placed on concave surface 126, and needle assembly 200 is pushed down the sloped concave surface 126 until the distal end of needle 206 punctures the skin of the forearm FA at the insertion site 170 at the desire angle of insertion θ set by the sloped section 122 to form a needle puncture 172 in the skin. The tubing 208 of the needle assembly 200 can be seated along the top surface of the rounded section 124 of protrusion 120.

FIG. 9 illustrates the forearm FA after device 100 and needle assembly 200 have been removed after completing the dialysis treatment. As shown, left on the skin of the patient are marks 108a-112a. In a subsequent dialysis treatment, the practitioner can align each hole 108-112 with its corresponding mark 108a-112a to ensure the needle 206 is inserted into the same needle puncture 172 that it was in the prior use of device 100. Additionally, by using device 100 for the subsequent treatment, the practitioner ensures that the needle 206 is inserted into puncture 172 at the same angle of insertion θ that it was in the prior use of device 100 which formed the initial puncture 172.

Although FIGS. 8 and 9 illustrate device 100 being used on the arm of a patient, those with skill in the art will understand that device 100 can be used on various body parts of the patient, and specifically can be used on various bodies parts where an AV fistula is traditionally formed for dialysis treatment. For example, device 100 can be used on the upper arm, calf, upper leg, pelvic area, and other areas of the patient's body.

Figure 10:
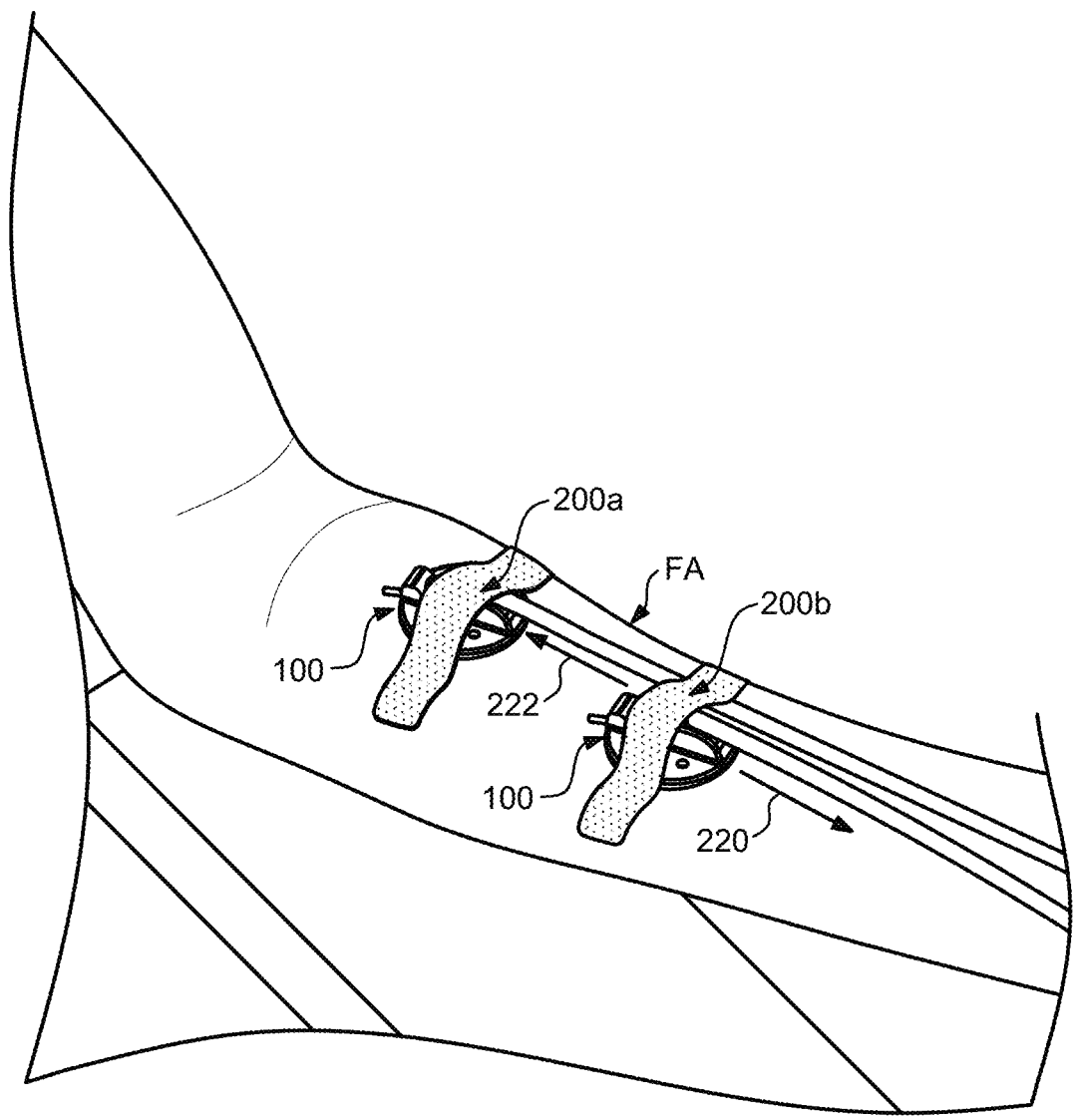
FIG. 10 illustrates two of the devices of FIG. 1 in use on a patient, each with a needle assembly.

FIG. 10 is included to illustrate how two of devices 100 can be used to perform a dialysis treatment. Specifically, two needle assemblies 200a, 200b are inserted into the AV fistula of a patient's forearm FA using devices 100, as has been previously described. Blood is drawn from the patient with needle assembly 200b along path 220 and sent to a dialysis machine for cleansing/treatment. Then, the treated blood is received from the dialysis machine along path 222 and inserted back into the AV fistula of the patient using needle assembly 200a. Devices 100 are configured to stay in place on the forearm FA while dialysis treatment is taking place. Although one purpose of device 100 is for aiding in the placement and insertion of the needle, another is to hold the needle assembly in position during a medical treatment, such as dialysis treatment. By keeping the needle in the skin of the user at the insertion angle θ, the device 100 prevents the needle from tugging at the skin/AV fistula that would occur if the needle assembly were simply taped flat against the skin, and thereby prevents damage to the associated insertion puncture 172. As shown, in some embodiments, medical tape can be placed across the top of the needle assembly and device 100 to further hold the device 100 and needle assembly 200a, 200b in place while the dialysis treatment is taking place.

Figure 11A:
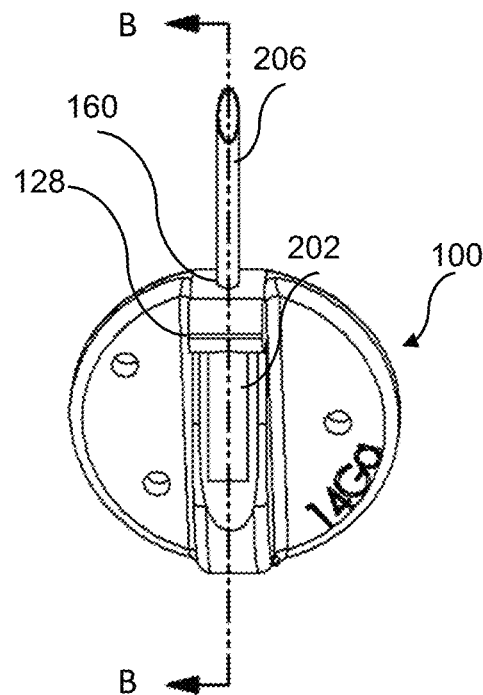
FIGS. 11A and 11B illustrate top and sectional views, respectively, of a medical needle seated in the device of FIG. 1.
Figure 11B:
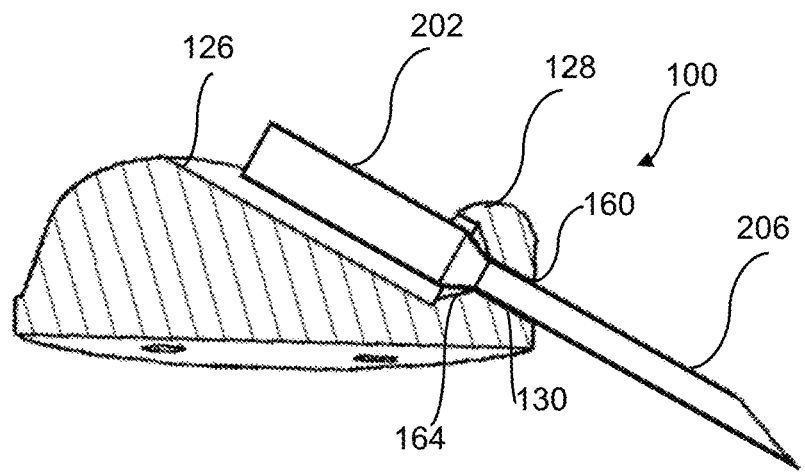

FIG. 11A illustrates a top view of device 100 with needle assembly hub 202 and needle 206 seated therein, and FIG. 11B is a cut view taken along section line B-B of FIG. 11A. As previously discussed, in the seated position, in some embodiments, the base of hub 202 is seated in conical section 164 and needle 206 passes through channel 130. Thus, needle 206 can be inserted into a patient at the insertion angle θ and remain seated at insertion angle θ during the medical activity, as discussed herein.

Figure 12A:
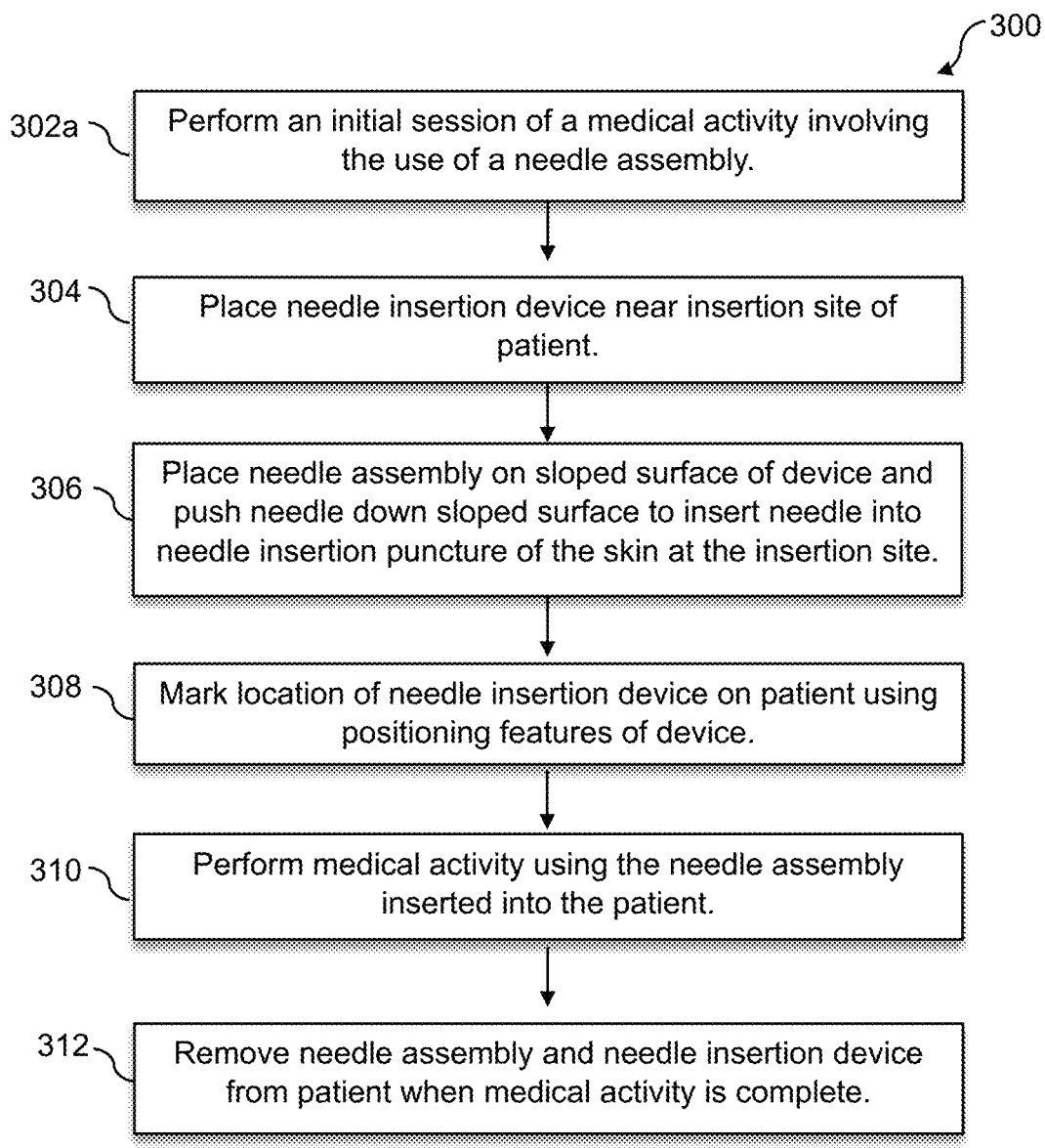
FIGS. 12A and 12B illustrate a method of placing and inserting a medical needle into a patient, according to an embodiment of this disclosure.
Figure 12B:
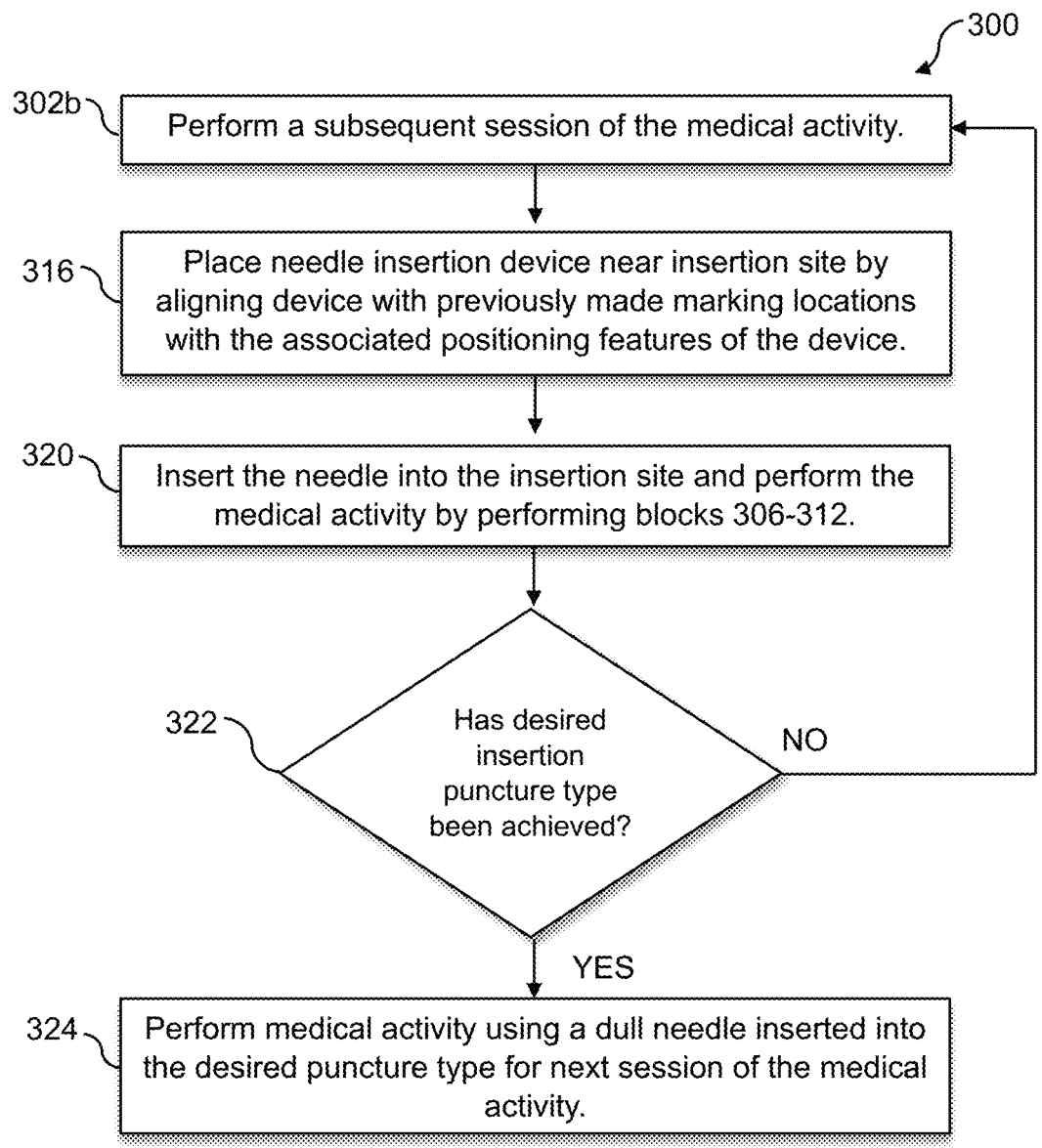

FIGS. 12A and 12B illustrate a method 300 of inserting a needle into a patient for performing a medical procedure or treatment using a needle placement and insertion device according to an embodiment of this disclosure, such as device 100, for example. As shown, method 300 comprises performing an initial session of treatment 302a, and also performing a subsequent treatment of the medical treatment 302b. For example, according to various embodiments, method 302a comprises performing an initial dialysis treatment at 302a, and performing a subsequent dialysis treatment at 302b. Those with skill in the art will recognize that dialysis patients often require multiple dialysis treatments every week, often for the rest of their lives or until they can receive a kidney transplant (thus, requiring numerous "subsequent treatments"). Thus, subsequent treatments 302b may be performed weeks, days, or hours within each other or the initial treatment 302a.

Accordingly, method 300 can begin at method 302a by performing an initial medical treatment, activity, or procedure on the patient, such as a dialysis treatment. Method 300 can continue at block 304 by placing device bottom surface 104 on the patient with the front end 114 adjacent to the needle insertion site, such as insertion site 170, as has been previously discussed. Method 300 can continue to block 306 by placing a sharp needle assembly 200 on concave surface 126 with the needle 206 facing channel 130, pushing the needle assembly down the slope of concave surface 126, and ultimately inserting the sharp distal end or tip of needle 206 into the patient at the insertion angle θ to form needle puncture 172, according to the descriptions above. As discussed, this can include inserting the needle into the AV fistula of a patient. In some embodiments, the needle assembly 200 is pushed until needle hub 202 contacts channel block 128 and/or is seated in channel conical section 164. In dialysis treatments, block 306 can further comprise confirming that cannulation was successful. Method 300 can continue to block 308 by using holes 108-112 to mark the desired location of device on the patient. Specifically, a practitioner passes a marking device through each hole 108-112 to form marks 108a-112a on the skin of the patient. Specifically, after a successful cannulation has been performed and confirmed in block 306, marks can be formed in block 308 to mark the location of the device 100 to mark the spot in which the device 100 was used for a successful cannulation. Various marking devices fall within the scope of this disclosure, such as, for example, an ink pen, marker, medical-grade marker, or medical-grade tattoo pen, for example, or any combination thereof. Method 300 can continue to block 310 by performing the medical activity, such as performing the dialysis treatment, for example, with the device remaining in place on the patient during the treatment. Method 300 can continue to block 312 by removing the needle assembly 200 and device 100 when the initial session of medical activity, procedure, or treatment, such as the dialysis treatment, is completed.

Those with skill in the art will understand that blocks 304-312 of the initial session 302a can be performed multiples time for any given initial session. For example, referring to FIG. 10, in performing a dialysis treatment, blocks 304-312 can be performed for each of the needle assemblies 200a, 200b required for the dialysis treatment. Additionally, while the initial session 302a is shown occurring in a certain order, those with skill in the art will understand that blocks 304-312 can be performed in any of a number of orders without departing from the scope of this disclosure. For example, in some embodiments, creating the marks 108a-112a in block 308 can be performed at a different order in the initial session, such as, for example, before the puncture 172 is formed (block 306) or after the medical activity has been performed (block 310) before the device 100 is removed from the patient. Additionally, those with skill in the art will recognize that various steps can be added or removed from block 304-312 without departing from the scope of this disclosure.

Referring to FIG. 12B, as mentioned, method 300 further comprises performing a subsequent session 302b of the medical activity, procedure, or treatment performed in the initial session 302a. As mentioned, dialysis patients are required to routinely receive dialysis treatments, and thus 302b can be any of the treatments following the initial treatment 302a performed with device 100. Method 300 can continue from block 302b to block 316 by placing device 100 on the patient such that each hole 108-112 is aligned with its associated mark 108a-112a. That is to say, in the desired placement and orientation of device 100, each mark 108a-112a is visible to the practitioner through the top of its associated hole 108-112. Thus, by the actions taken in block 316, the practitioner can be sure the device 100 is positioned in the same placement and orientation as the device was in the initial treatment 302*a*, and ultimately ensures the needle 206 is inserted into the existing puncture location 172 at the same insertion angle θ. Method 300 can continue to block 320 by inserting the sharp needle 206 into the patient's skin and performing the medical activity, such as dialysis treatment, by performing blocks 306-312 previously described. Thus, in block 320, because the device 100 is in the same position and orientation as it was in the initial session 302*a*, and since the same device 100 is used, the needle 206 is inserted in the subsequent session 302*b* into the same puncture location 172 at the same angle of insertion θ as it was in the initial session 302*a*. In block 320, a practitioner can optionally re-mark each location 108*a*-112*a* using the same methods described in block 308. The re-marking of each location 108*a*-112*a* is described as optional because, in some subsequent treatments, the practitioner may determine the previously made marks are sufficiently dark and do not require re-marking. For example, if the previously made marks 108*a*-112*a* are made the day before with permanent ink, or if the previously made marks 108*a*-112*a* were made with a tattoo pen, re-marking of the marks may not be necessary. Method 300 can continue to block 322 by determining if puncture location 172 has been transformed into a desired insertion puncture type, such as if the puncture has transformed into a sufficient button hole puncture. In response to determining that the puncture 172 is not a sufficient buttonhole, the next time the patient needs dialysis treatment, the practitioner can perform another subsequent session with a sharp needle at block 302*b*. In response to determining that location has been sufficiently transformed to a buttonhole sufficient for performing the buttonhole technique, the method can continue to block 324, where the next dialysis treatment required for the patient is performed using a dull dialysis needle being inserted into the buttonhole formed at location of puncture 172.

Those with skill in the art will understand that blocks 316-324 of the subsequent session 302*b* can be performed multiples time for any given initial session. For example, referring to FIG. 10, for a dialysis treatment, blocks 316-324 can be performed for each of the needle assemblies 200*a*, 200*b* required for the dialysis treatment. Additionally, while the subsequent session 302*b* is shown occurring in a certain order, those with skill in the art will understand that blocks 316-324 can be performed in any of a number of orders without departing from the scope of this disclosure. Additionally, those with skill in the art will recognize that various steps can be added or removed from block 316-324 without departing from the scope of this disclosure.

As those with skill in the art will understand, and as previously discussed, traditionally performing buttonhole technique involves a skilled practitioner inserting a sharp dialysis needle into the same puncture location at the same insertion angle routinely over numerous treatment sessions until the puncture location is transformed into a tunneled track in the patient's skin. Eventually, this tunnel becomes formed enough that a practitioner can insert a dull dialysis needle through this tunnel (i.e. a "buttonhole"), which is much less painful than creating a new puncture with a sharp needle for every treatment, and also prevents damage to the AV fistula.

Thus, the buttonhole technique is difficult to achieve, as it requires the practitioner to insert the sharp dialysis needle into the exact same location every session at the same insertion angle in order to form the buttonhole, which requires the practitioner to have a high-degree of practice and experience with this technique. Accordingly, method 300 and device 100 can be used to efficiently and effectively form buttonhole punctures on the dialysis patient. As described, device 100 ensure that, for each treatment session performed on a patient (blocks 302*a*, 302*b*), the practitioner inserts the sharp needle 206 into the same location 172, at the same orientation, and at the same insertion angle θ every treatment session to more efficiently form the desired buttonhole at the location 172. Additionally, device 100 enables practitioners with less skill or experience in performing the buttonhole technique the ability to safely and easily provide this treatment to their patients.

Although method 300 has been described herein as being performed by a healthcare provider or practitioner, those with skill in the art will recognize that method 300 can be performed using device 100 by many types of individuals. For example, one benefit of device 100 is that it enables those with little to no formal medical training to administer dialysis to a patient who would not be able to otherwise. For example, method 300 can be performed on patient for in-home dialysis treatment, rather than at a clinic by a healthcare practitioner. Device 100 enables someone such as a caregiver or family member to perform dialysis treatment on the patient in the comfort of their home. Additionally, in many cases, the patient themselves can easily administer in-home dialysis treatment to themself with the use of device 100 and parts or all of method 300. Device 100 enables a patient to be able to administer treatment to themselves using only one hand, which would not be possible otherwise.

Figure 13:
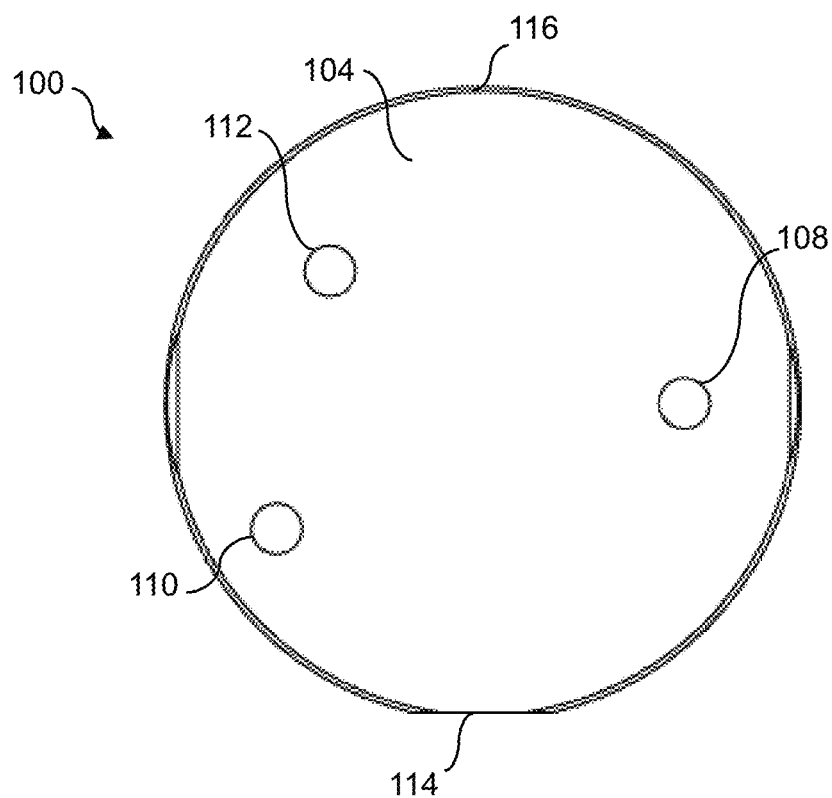
FIG. 13 illustrates a bottom side view of the device of FIG. 1.
Figure 14:
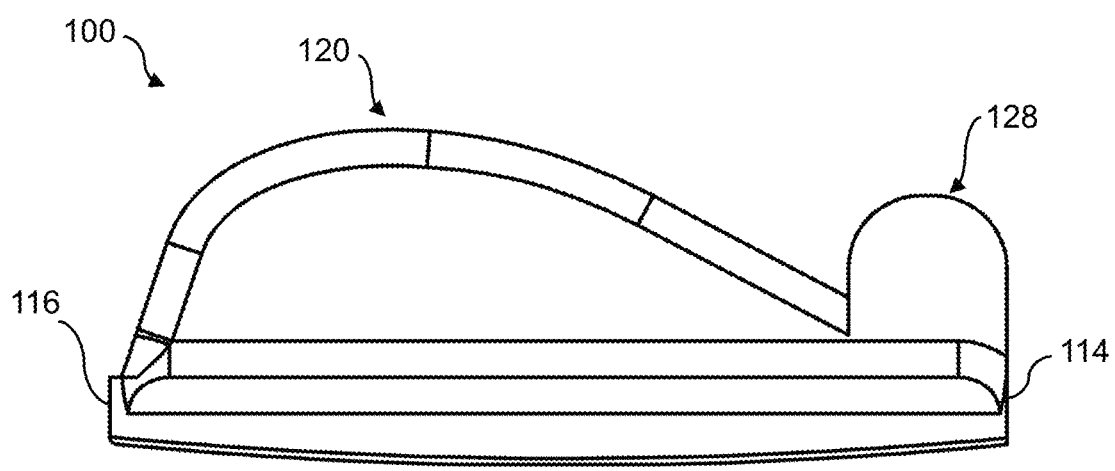
FIG. 14 illustrates a right side view of the device of FIG. 1.

FIG. 13 illustrates a bottom side view of device 100, specifically illustrating bottom surface 104 and through holes 108-112. FIG. 14 illustrates a right side view of device 100, specifically illustrating protrusion 120 and channel block 128. As will be understood by those with skill in the art, protrusion 120 and channel block 128 are substantially symmetrical along a center length axis of device 100 spanning from front end 114 to rear end 116 such that FIG. 14 is substantially a mirror-image of the left side view of device 100 in FIG. 3. FIGS. 13 and 14 are included so that each side of device 100 is fully depicted by this disclosure.

Figure 15:
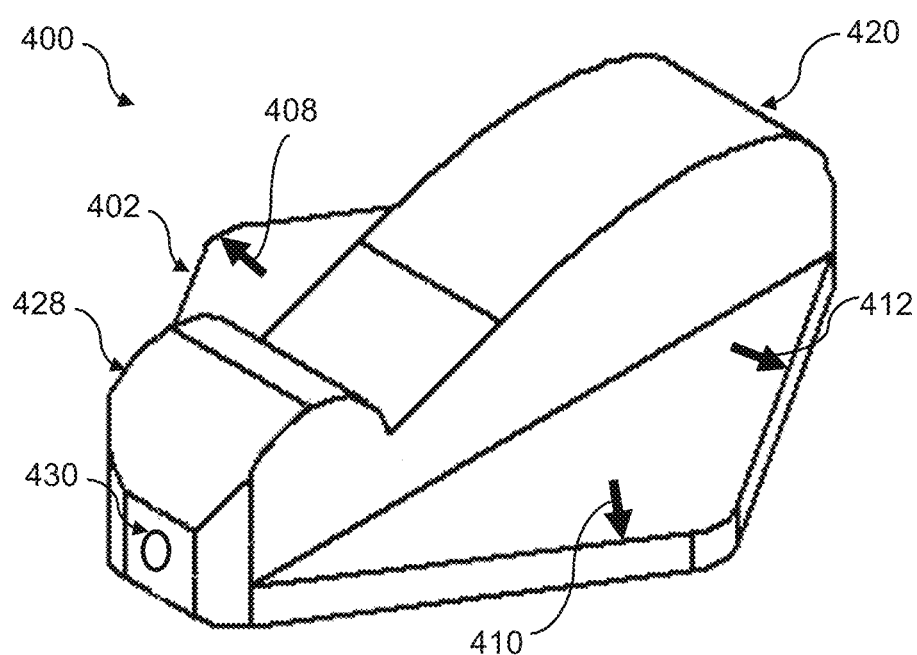
FIG. 15 illustrates a perspective view of a medical needle placement and insertion device, according to another embodiment of this disclosure.

FIG. 15 illustrates a perspective view of a needle insertion device 400, substantially similar to device 100 previously discussed. Specifically, device 400 is substantially the same as device 100 except for the shape of its base 402. As shown device 100 has a rhombus or diamond shaped base 402 rather than circular base 102. Otherwise, device 400 comprises a needle guidance protrusion 420 (substantially the same as protrusion 120); a channel block 428 (substantially the same as block 128); a needle channel 430 (substantially the same as channel 130); and a plurality of positioning arrows 408-412 (serving substantially the same purpose as through-holes 108-112). As those with skill in the art will understand, the methods described herein, such as method 300, can be performed using device 400.

As previously mentioned, positioning features of the devices herein can be any of a number of feature-types, such as positioning arrow 408-412, embossed, engraved, or elevated on the top surface of base 402. Once in a position, the practitioner can form a mark on the skin along the edge of base 402 adjacent to each arrow 408-412. Thus, in subsequent uses of device 400, each arrow 408-412 can be aligned with its associated, previously-made mark, for positioning and aligning device 100, much in the same way holes 108-112 are aligned with their associated marks, as has been described in great detail. Accordingly, those with skill in the art will recognize that various feature-types can be used for positioning and alignment features according to various embodiments of this disclosure.

Although devices 100, 400 with circular and rhombus bases 102, 402 have been described, those with skill in the art will understand that various embodiments of devices disclosed herein include bases of varying geometries. For example, included in this disclosure are devices with bases shaped substantially triangular, square, rectangular, oval, elliptical, pentagonal, hexagonal, heptagonal, octagonal, cross-shaped, and star-shaped. However, bases of devices herein can comprise any of a number of other shapes without departing from the scope of this disclosure.

According to various embodiments, device 100, 400 is made from a single piece of hard plastic suitable and sterilized for medical applications. For example, in some embodiments, device 100, 400 is made from a medical grade polymer material. According to some embodiments, device 100, 400 is made from any known method of producing such single-pieced plastic objects, such as 3D printing or injection molding, for example. As previously mentioned, according to various embodiments, devices 100, 400 can be made of varying colors of plastic, the color of the device depending on the size of the needle meant to the used with the specific device 100, 400. According to various embodiments, device 100, 400 is made from a single piece of metallic or rubber material.

Those with skill in the art will recognize the improvements devices 100, 400 bring to the medical industry, and especially for dialysis treatments. First, as has been described in great depth, the device 100, 400 enables the practitioner to insert a needle into a patient at the same location, angle, and orientation over a span of multiple treatment sessions, which is very desirable for practitioners forming buttonhole punctures for dialysis treatments. Additionally, device 100, 400 enable the practitioner to keep the needle in the puncture at the insertion angle while blood is being drawn/injected. Traditionally, in order to keep a needle at a desired angle during blood draw/injection, practitioners place a cotton ball or similar item between the forearm and the needle assembly to maintain an angle between needle assembly and the forearm to prevent damage to the skin/vein/artery/AV fistula and also to prevent discomfort/pain to the patient. These traditional practices do not always serve their intended purposes, as this way of keeping the needle propped up is very unstable and unreliable. Device 100, 400 can be kept in place while blood is being drawn/injected and thus maintain a stable and reliable angle of insertion θ to prevent damage or discomfort to the patient. Thus, although dialysis treatment has been described in detail, device 100, 400 and the associated methods, such as method 300, herein can be used for any medical treatment or activity involving the drawing or injection of blood or any other substance typically drawn from or injected into patients. Additionally, as those with skill in the art will recognize. device 100, 400 can be used for various other medical purposes, such as, for example, drawing/injecting plasma from/to a patient.

Although the present invention has been described in terms of the foregoing disclosed embodiments, this description has been provided by way of explanation only and is not intended to be construed as a limitation of the invention. Indeed, even though the foregoing descriptions refer to numerous components and other embodiments that are presently contemplated, those of ordinary skill in the art will recognize many possible alternatives exist that have not been expressly referenced or even suggested here. While the foregoing written descriptions should enable one of ordinary skill in the pertinent arts to make and use what are presently considered the best modes of the invention, those of ordinary skill will also understand and appreciate the existence of numerous variations, combinations, and equivalents of the various aspects of the specific embodiments, methods, and examples referenced herein.

Hence the drawings and detailed descriptions herein should be considered illustrative, not exhaustive. They do not limit the invention to the particular forms and examples disclosed. To the contrary, the invention includes many further modifications, changes, rearrangements, substitutions, alternatives, design choices, and embodiments apparent to those of ordinary skill in the art, without departing from the spirit and scope of this invention.

Accordingly, in all respects, it should be understood that the drawings and detailed descriptions herein are to be regarded in an illustrative rather than a restrictive manner and are not intended to limit the invention to the particular forms and examples disclosed. In any case, all substantially equivalent systems, articles, and methods should be considered within the scope of the invention and, absent express indication otherwise, all structural or functional equivalents are anticipated to remain within the spirit and scope of the presently disclosed systems and methods.

What is claimed is:

1. A device for positioning and inserting a needle assembly into a patient, comprising:
    a base including:
        a bottom surface configured to contact the skin of the patient,
        a top surface opposite of the bottom surface,
        a front end configured to be placed adjacent to a needle insertion site of the patient,
        a rear end opposite of the front end, and
        a plurality of positioning features configured to be used for positioning and aligning the device on the patient;
    a needle channel disposed on the top surface adjacent to the front end and comprising a channel outlet facing the front end and a channel inlet opposite the channel outlet; and
    a needle guidance protrusion disposed on the top surface and including a sloped surface having a first end disposed adjacent to the channel inlet and a second end displaced from the first end toward the direction of the rear end of the base, wherein the sloped surface is sloped at a slope angle such that the second end is disposed at a greater elevation from the top surface of the base than the first end,
    wherein the needle assembly is configured to be placed on the sloped surface and pushed down the sloped surface such that a needle of the needle assembly travels through the needle channel to the needle insertion site to form an insertion puncture in the skin of the patient.

2. The device of claim 1, wherein the slope angle is substantially between 15 and 45 degrees from the base.

3. The device of claim 1, wherein:
    the needle guidance protrusion further comprises a convex rounded section extending from the second end of the sloped surface to the rear end of the base; and
    a tube of the needle assembly is configured to be placed along a top of the convex rounded section.

4. The device of claim 3, wherein the convex rounded section comprises:
    a first convex section extending from the second end of the sloped section;
    a second convex section extending from the first convex section and being more rounded than the first convex section, wherein the second convex section comprises the apex of the needle guidance protrusion; and a tail section extending from the second convex section towards the rear end of the base, wherein the tail section is relatively flat in comparison to the first and second convex sections.

5. The device of claim 1, wherein the sloped surface comprises a concave top surface for receiving the needle assembly.

6. The device of claim 1, wherein the bottom surface of the device is concave to accommodate the curvature of the body part of the patient on which the device is placed.

7. The device of claim 6, wherein the bottom surface is concave about an axis spanning from the front end of the base to the rear end of the base.

8. The device of claim 1, wherein the bottom surface comprises, or is configured to be used with, an adhesive for adhering the device to the skin of the patient.

9. The device of claim 1, wherein the base has a generally circular cross-section.

10. The device of claim 1, wherein:

each of the plurality of positioning features is a through-hole spanning from the top surface to the bottom surface of the base;

each of the plurality of through-holes is sized to allow for a user to pass a marking device through the through-hole and create a mark on the skin of the patient associated with the through-hole.

11. The device of claim 10, wherein the plurality of through-holes are positioned on the base such that aligning each of the through-holes with an associated and previously-made mark of the through-hole results in the device being positioned on the patient in a place proper using the device to insert the needle assembly into the insertion puncture.

12. The device of claim 10, wherein:

there are three of the plurality of through-holes;

two of the plurality of through-holes are disposed on a first side of the needle guidance protrusion; and one of the plurality of through-holes is disposed on a second side of the needle guidance protrusion.

13. The device of claim 1, wherein:

the channel outlet has a smaller diameter than the channel inlet;

the channel outlet is part of a channel cylindrical section of the needle channel;

the channel inlet is part of a conical section of the needle channel, wherein the conical section is configured to reduce the diameter of the needle channel from the diameter of the channel inlet to the diameter of the channel outlet.

14. The device of claim 1, wherein the needle channel is disposed in a channel block disposed on the top surface of the base adjacent to the front end of the base.

15. The device of claim 14, wherein the channel block has a convex round top surface.

16. The device of claim 1, wherein the device is formed from a single piece of plastic material.

* * * * *